(12) United States Patent
Park et al.

(10) Patent No.: US 8,012,322 B2
(45) Date of Patent: Sep. 6, 2011

(54) BIOSENSOR FOR DISEASE DIAGNOSIS

(75) Inventors: Young Nam Park, Yongin-Si (KR); Rak Sun Mok, Busan-Si (KR); Myoung Kyu Kim, Suwon-Si (KR)

(73) Assignees: Yeongdong Dianostics Corporation, Yongin-Si, Kyunggi-Do (KR); Yeongdong Electronics Co., Ltd., Yongin-Si, Kyunggi-Do (KR)

( * ) Notice: Subject to any disclaimer, the term of this patent is extended or adjusted under 35 U.S.C. 154(b) by 0 days.

(21) Appl. No.: 12/050,815

(22) Filed: Mar. 18, 2008

(65) Prior Publication Data

US 2008/0277278 A1    Nov. 13, 2008

(51) Int. Cl.
*G01N 27/327* (2006.01)

(52) U.S. Cl. ............... 204/403.04; 204/403.03

(58) Field of Classification Search . 204/403.01–403.15
See application file for complete search history.

(56) References Cited

U.S. PATENT DOCUMENTS

| 5,437,999 | A  | * | 8/1995 | Diebold et al. | .......... 204/403.11 |
| 6,592,745 | B1 | * | 7/2003 | Feldman et al. | ........... 205/777.5 |
| 7,022,218 | B2 | * | 4/2006 | Taniike et al. | ............. 205/777.5 |
| 2004/0043477 | A1 | * | 3/2004 | Schibli | ....................... 435/287.1 |

* cited by examiner

*Primary Examiner* — Alex Noguerola
(74) *Attorney, Agent, or Firm* — Birch, Stewart, Kolasch & Birch, LLP

(57) ABSTRACT

The present invention relates to a biosensor including: a bottom plate having a base film having a lead mounted at one side of the top surface thereof, an electrode member formed on the base film, a spacer formed on the top surface of the electrode member so as to secure a recess having a predetermined width formed on the electrode member, and an enzyme reaction layer formed transversely on the top surface of the electrode member in such a fashion as to be positioned in the recess of the spacer; and a top plate formed integrally with the bottom plate and having the same configuration as the bottom plate.

9 Claims, 7 Drawing Sheets

BIOSENSOR FOR DISEASE DIAGNOSIS

BACKGROUND OF THE INVENTION

1. Field of the Invention

The present invention relates to a biosensor for disease diagnosis that employs an electrode to accurately check various diseases by using an electrode method, and more particularly, to a biosensor that is provided with electrode members disposed on a bottom plate and on a top plate, respectively, such that the electrode members are opposite to each other so as to enable the combined use of working electrodes and counter electrodes, thereby enhancing the convenience in use and the accuracy of the diagnosis.

2. Background of the Related Art

Methods for measuring a disease that have been widely used largely include colormetry using a strip and a biosensor using electrodes. Particularly, the biosensor using electrodes is popularly used.

According to the reaction principle of the electrode method, the biosensor includes an enzyme reacting with glucose and a substance generating an electrical signal from the reaction such that if blood is injected into the biosensor, the enzyme in the biosensor is reacted with the glucose in the blood to generate the electrical signal therefrom, and the electrical signal is received in a measuring device so as to display a concentration of the substance by the operation of an internal program. At this time, an amperometric method is usually adopted as a method for measuring the electrical signal.

The enzyme reaction process will be described below.

Gluconic acid and a reduced enzyme are produced by using glucose oxidase (hereinafter, referred to as 'GO') that can oxidize glucose, and an electric current emitted as the reduced enzyme is oxidized by an electronic medium is measured, thereby measuring a blood glucose level.

Ferrocyanide→Ferricyanide+e—
GO/FADH$_2$+O$_2$→GO/FAD+H$_2$O$_2$

At this time, it is found that oxygen rivals the electronic medium in the FADH on the electrode using the GO as the enzyme, thereby undesirably producing side reaction.

SUMMARY OF THE INVENTION

Accordingly, the present invention has been made in an effort to solve the above-mentioned problems occurring in the prior art, and it is an object of the present invention to provide a biosensor for disease diagnosis, which has electrode members formed on a bottom plate and on a top plate, respectively, such that the electrode members are opposite to each other so as to enable the combined use of working electrodes and counter electrodes.

It is another object of the present invention to provide a biosensor for disease diagnosis which has an enzyme reaction layer formed transversely on an electrode member such that even though blood is injected in every direction on a biosensor strip, the same measured values are obtained.

It is still another object of the present invention to provide a biosensor for disease diagnosis that allows an enzyme reaction solution to be pipetted on both surfaces of the top plate and the bottom plate, thereby preventing the generation of variation between the top plate and the bottom plate.

To accomplish the above objects, according to the present invention, there is provided a biosensor including: a bottom plate having a base film having a lead mounted at one side of the top surface thereof, an electrode member formed on the base film, a spacer formed on the electrode member so as to secure a recess having a predetermined width formed on the electrode member, and an enzyme reaction layer formed transversely on the top surface of the electrode member in such a fashion as to be positioned in the recess of the spacer; and a top plate formed integrally with the bottom plate and having the same configuration as the bottom plate.

According to the present invention, preferably, the base film is made of any one selected from heat-resistant polymers like polyethylene terephthalate (PET), polyethylene (PE) and polyvinyl chloride (PVC).

According to the present invention, preferably, the electrode member is formed of a conductive material like carbon, copper, gold, silver, platinum or palladium.

According to the present invention, preferably, an enzyme reaction solution is pipetted on the recess formed on the spacer of each of the top plate and the bottom plate, thereby preventing the generation of variations between the top plate and the bottom plate.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIGS. 1a and 1b are plan views showing an electrode member formed on a base film in a biosensor according to the present invention, wherein FIG. 1a shows the configuration of a bottom plate and FIG. 1b shows that of a top plate;

FIG. 2b shows that of the top plate;

DETAILED DESCRIPTION OF THE PREFERRED EMBODIMENT

Hereinafter, an explanation on a biosensor according to a preferred embodiment of the present invention will be given with reference to the attached drawings.

Figure 1A:
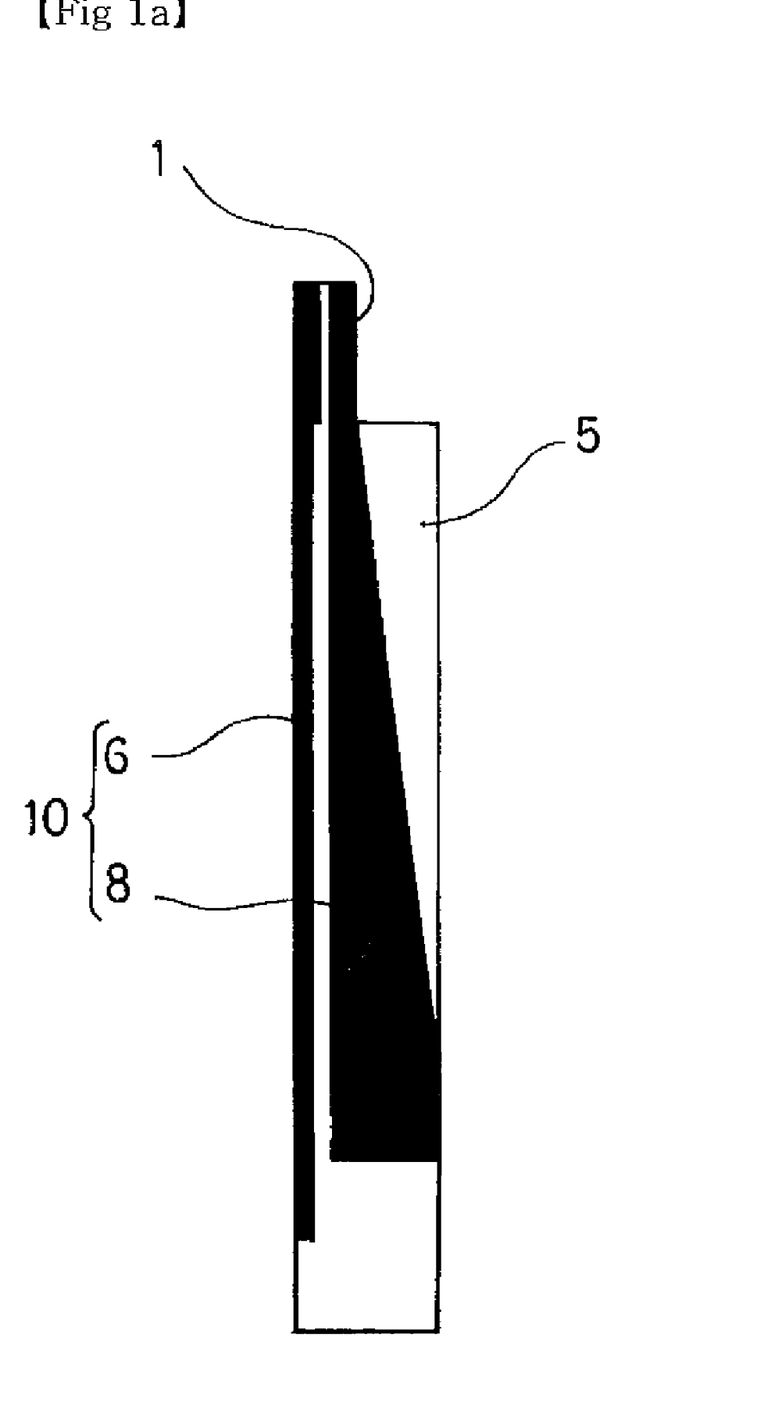
Figure 1B:
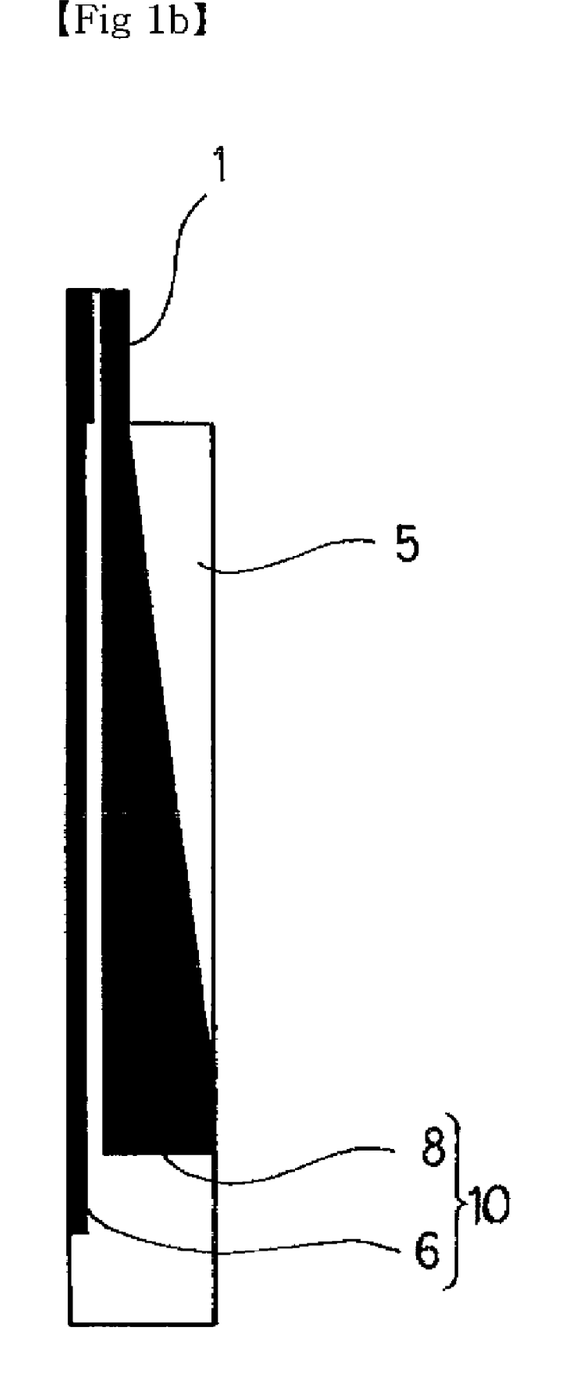
Figure 2A:
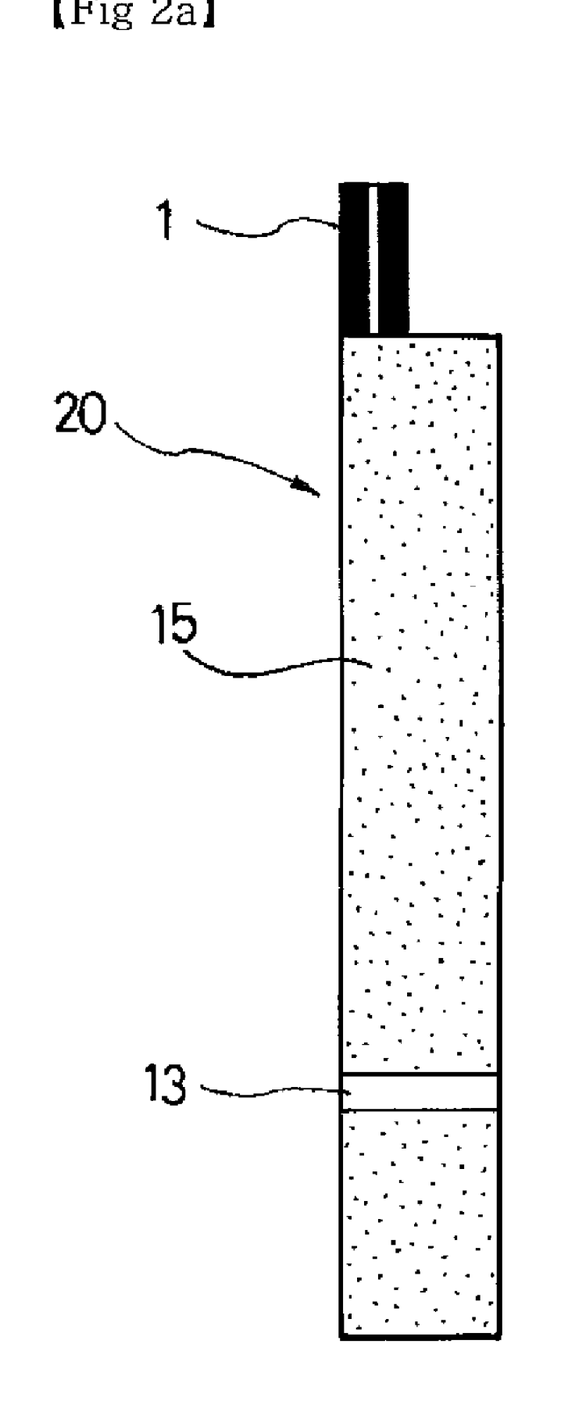
FIGS. 2a and 2b are plan views showing a spacer formed on the electrode member in the biosensor according to the present invention, wherein FIG. 2 a shows the configuration of the bottom plate
Figure 2B:
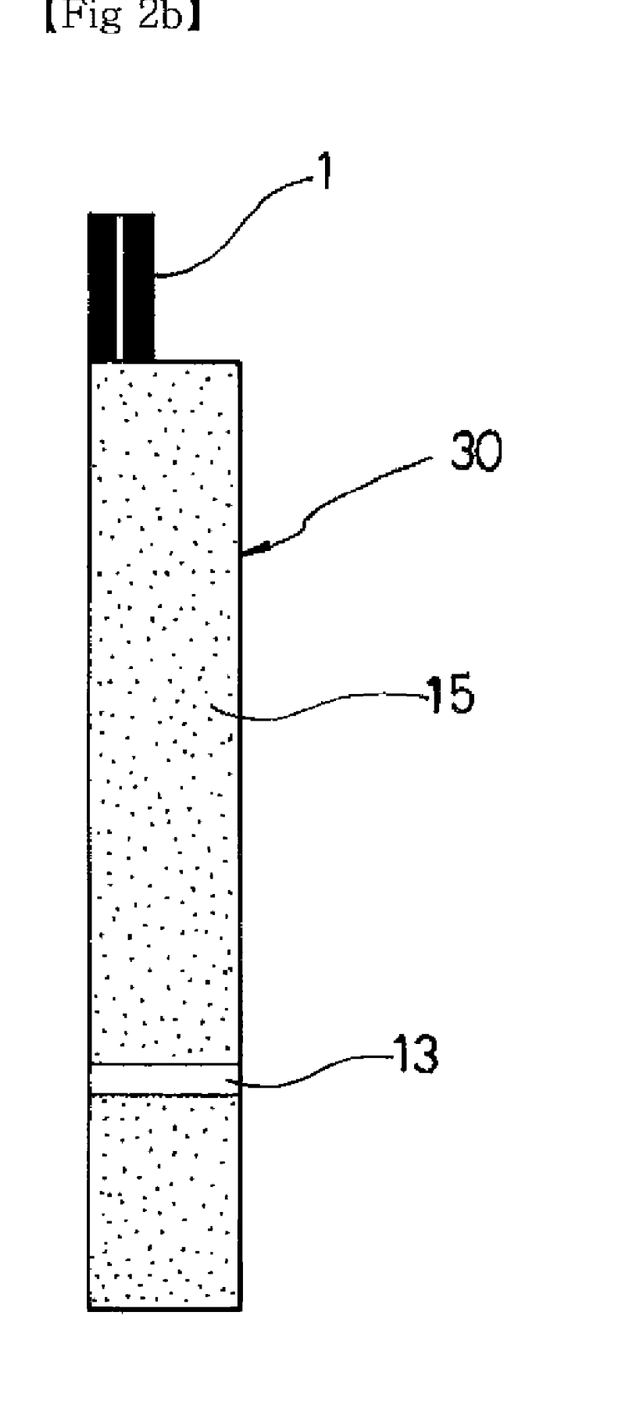
Figure 3:
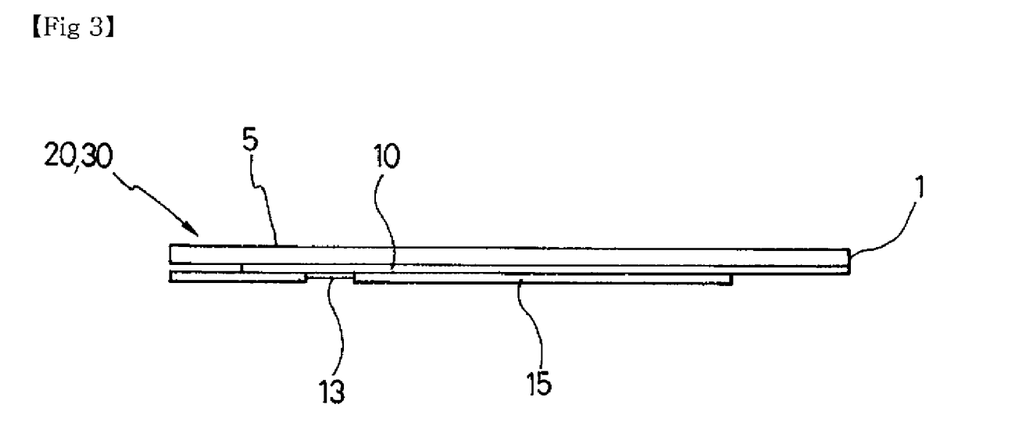
FIG. 3 is a side view of the bottom or top plate in the biosensor according to the present invention.
Figure 4:
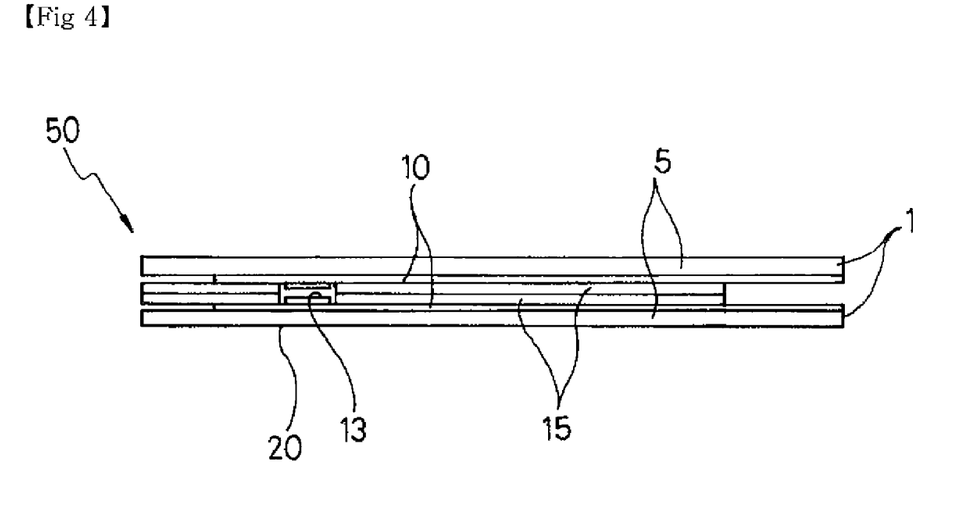
FIG. 4 is a side view showing the assembled state between the bottom plate and the top plate in the biosensor according to the present invention.
Figure 5:
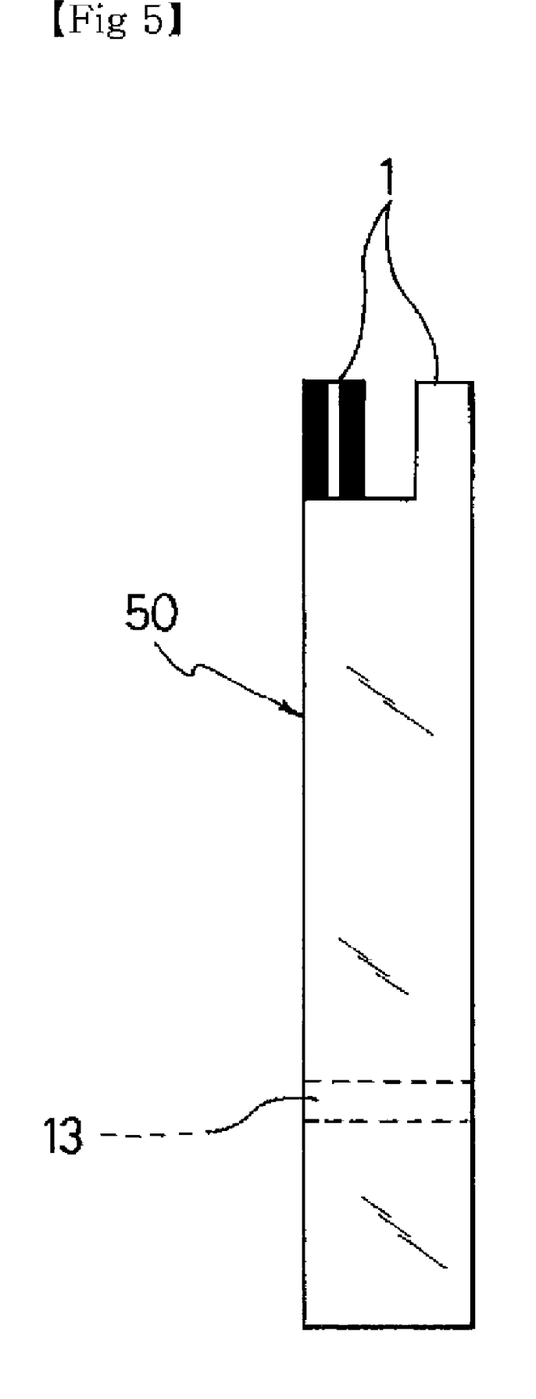
FIG. 5 is a plan view showing the assembled state between the bottom plate and the top plate in the biosensor according to the present invention.

FIGS. 1a and 1b are plan views showing an electrode member formed on a base film in a biosensor according to the present invention, wherein FIG. 1a shows the configuration of a bottom plate and FIG. 1b shows that of a top plate, FIGS. 2a and 2b are plan views showing a spacer formed on the electrode member in the biosensor according to the present invention, wherein FIG. 2a shows the configuration of the bottom plate and FIG. 2b shows that of the top plate, FIG. 3 is a side view of the bottom or top plate in the biosensor according to the present invention, FIG. 4 is a side view showing the assembled state between the bottom plate and the top plate in the biosensor according to the present invention, and FIG. 5 is a plan view showing the assembled state between the bottom plate and the top plate in the biosensor according to the present invention.

According to the present invention, as shown, there is provided a biosensor including: a bottom plate 20 having a base film 5, an electrode member 10 formed on the base film 5, and a spacer 15 formed on the top surface of the electrode member 10; and a top plate 30 formed integrally with the bottom plate 20 and having the same configuration as the bottom plate 20.

The base film 5 has a lead 1 having a generally narrow width protruded outwardly from one side of the top surface thereof, and it is preferably made of any one selected from heat-resistant polymers like polyethylene terephthalate (PET) polyethylene (PE) and polyvinyl chloride (PVC).

The electrode member 10 that is formed on the top surface of the base film 5 has a blood check electrode 6 and a check electrode 8 spaced apart from each other.

The electrode member 10 is formed of a conductive material like carbon, copper, gold, silver, platinum or palladium.

An enzyme reaction layer 13 having a predetermined width is formed transversely on the top surface of the electrode member 10, which is defined by the formation of the spacer 15.

That is, the spacer 15 is formed on the top surface of the electrode member 10, while securing a recess having a predetermined width formed transversely on the electrode member 10, and after that, an enzyme reaction solution is pipetted and dried on the recess formed on the spacer 15, thereby forming the enzyme reaction layer 13.

The top plate 30 is formed integrally with the bottom plate 20, while having the same configuration as the bottom plate 20 excepting that the blood check electrode 6 and the check electrode 8 of the electrode member 10 are disposed on the base film 5 in a reverse order to the bottom plate 20.

As the bottom plate 20 and the top plate 30 are bonded integrally with each other, the biosensor 50 is completely manufactured, and at this time, the leads 1 mounted at the bottom plate 20 and the top plate 30 are arranged three-dimensionally in such a manner as to be opposite to each other.

At this time, the leads 1 of the bottom plate 20 and the top plate 30 are spaced apart from each other by a distance ranging between 1.5 mm and 2 mm, which are adapted to be inserted into a measuring device for checking a disease. In this case, the leads 1 are formed bi-directionally, which enables rapid checking.

As described above, there is provided the biosensor having the electrode member formed on the bottom plate and the top plate, respectively, such that the electrode members are opposite to each so as to enable the combined use of working electrodes and counter electrodes, and the enzyme reaction layer formed transversely on the electrode member such that even though blood is injected in every direction on the biosensor strip, the same measured values are obtained. Further, the biosensor of this invention can allow the enzyme reaction solution to be pipetted on the both of the top plate and the bottom plate, thereby preventing the generation of variation between the top plate and the bottom plate.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A biosensor for disease diagnosis using an electrode, comprising:
   a bottom plate including,
      a first base film having a first lead mounted at one side of the top surface thereof,
      a first electrode member formed on the first base film, one side of the first electrode member being the first lead,
      a first spacer formed on the top surface of the first electrode member so as to secure a first recess having a predetermined width formed on the first electrode member, and
      a first enzyme reaction layer formed transversely on the top surface of the first electrode member in such a fashion as to be positioned in the first recess of the first spacer; and
   a top plate formed integrally with the bottom plate and including,
      a second base film having a second lead mounted at one side of the top surface thereof,
      a second electrode member formed on the second base film,
      a second spacer formed on the top surface of the second electrode member so as to secure a second recess having a predetermined width formed on the second electrode member, and
      a second enzyme reaction layer formed transversely on the top surface of the second electrode member in such a fashion as to be positioned in the second recess of the second spacer,
   wherein the first and second base films are made of any one selected from heat-resistant polymers like polyethylene terephthalate (PET), polyethylene (PE) and polyvinyl chloride (PVC),
   the first spacer and the second spacer contact each other, and
   the first recess is formed transversely across the first base film from one lateral side of the first base film to an opposite lateral side of the first base film, and the second recess is formed transversely across the second base film from one lateral side of the second base film to an opposite lateral side of the second base film.

2. The biosensor according to claim 1, wherein the first and second electrode members are formed of a conductive material like carbon, copper, gold, silver, platinum or palladium.

3. The biosensor according to claim 1, wherein an enzyme reaction solution is pipetted on the recess formed on the spacer of each of the top plate and the bottom plate, thereby preventing the generation of variations between the top plate and the bottom plate.

4. The biosensor according to claim 1, wherein the first enzyme reaction layer and the second enzyme reaction layer are spaced apart from each other.

5. The biosensor according to claim 1, wherein the first lead and the second lead are spaced apart from each other.

6. The biosensor according to claim 1, wherein the first lead and the second lead are in different planes.

7. The biosensor according to claim 1, wherein the first lead includes two electrodes spaced apart from each other and the second lead includes two electrodes spaced apart from each other.

8. The biosensor according to claim 1, wherein the first lead is a portion of the first electrode protruding outwardly away from the first base film and the second lead is a portion of the second electrode protruding outwardly away from the second base film.

9. A biosensor for disease diagnosis using an electrode, comprising:
   a bottom plate including,
      a first base film having a first lead mounted at one side of the top surface thereof,
      a first electrode member formed on the first base film, one side of the first electrode member being the first lead,
      a first spacer formed on the top surface of the first electrode member so as to secure a first recess having a predetermined width formed on the first electrode member, and
      a first enzyme reaction layer formed transversely on the top surface of the first electrode member in such a fashion as to be positioned in the first recess of the first spacer; and
   a top plate formed integrally with the bottom plate and including,
      a second base film having a second lead mounted at one side of the top surface thereof,
      a second electrode member formed on the second base film,
      a second spacer formed on the top surface of the second electrode member so as to secure a second recess having a predetermined width formed on the second electrode member, and
      a second enzyme reaction layer formed transversely on the top surface of the second electrode member in such a fashion as to be positioned in the second recess of the second spacer,
   wherein the first and second base films are made of any one selected from heat-resistant polymers like polyethylene terephthalate (PET), polyethylene (PE) and polyvinyl chloride (PVC),
   the first spacer and the second spacer contact each other, and
   the first enzyme reaction layer is formed transversely across the first base film from one lateral side of the first base film to an opposite lateral side of the first base film and is located entirely within the first recess, and the second enzyme reaction layer is formed transversely across the second base film from one lateral side of the second base film to an opposite lateral side of the second base film and is located entirely within the second recess.

* * * * *